(12) United States Patent
Copf et al.

(10) Patent No.: US 6,287,342 B1
(45) Date of Patent: Sep. 11, 2001

(54) PROSTHESIS PART

(76) Inventors: Franz Copf, Marienstrasse 12, D-70178 Stuttgart; Ulrich Holz, Don-Carlos-Strasse 23, D-70563 Stuttgart, both of (DE)

( * ) Notice: Subject to any disclaimer, the term of this patent is extended or adjusted under 35 U.S.C. 154(b) by 0 days.

(21) Appl. No.: 09/155,837

(22) PCT Filed: Apr. 2, 1997

(86) PCT No.: PCT/EP97/01647

§ 371 Date: Jun. 1, 1999

§ 102(e) Date: Jun. 1, 1999

(87) PCT Pub. No.: WO97/36559

PCT Pub. Date: Oct. 9, 1997

(30) Foreign Application Priority Data

Apr. 2, 1996  (DE) .............................................. 196 13 078

(51) Int. Cl.[7] ...................................................... A61F 2/28
(52) U.S. Cl. .................................. 623/16.11; 623/18.11; 623/22.11
(58) Field of Search .................................. 623/16, 18, 22, 623/23, 16.11, 22.11, 22.12, 22.4, 22.41, 23.21, 18.11

(56) References Cited

U.S. PATENT DOCUMENTS

| 4,770,660 | * | 9/1988 | Averill . | |
| 4,888,022 | * | 12/1989 | Huebsch | 623/22 |
| 4,904,262 | * | 2/1990 | Bensmann | 623/18 |
| 4,904,268 | * | 2/1990 | Alvarado | 623/22 X |
| 5,002,578 | * | 3/1991 | Luman | 623/18 X |
| 5,002,579 | * | 3/1991 | Copf et al. . | |
| 5,092,899 | * | 3/1992 | Forte | 623/18 X |
| 5,163,964 | * | 11/1992 | Lazzeri et al. . | |

* cited by examiner

Primary Examiner—Jeffrey A. Smith

(57) ABSTRACT

A prosthesis part can be implanted without the use of cement. The prosthesis part comprises: a cage structure, which unites with the spongy substance of the bone; a carrier plate which is connected to the cage structure; and a carrier post for a joint part. The carrier post is supported by the carrier plate. The carrier plate has openings through which a severing instrument, such as a chisel or milling cutter, is introducable in order to separate the cage structure at least to a large extent from the cortical substance of the bone.

6 Claims, 4 Drawing Sheets

PROSTHESIS PART

The invention relates to a prosthetic part to be implanted into the end of a thighbone adjacent to the hip joint.

A prosthetic part of this type is described in DE 37 07 518 A1.

After such a prosthetic part has been implanted, spongy substance grows between the anchorage pillars of the cage structure, as a result of which the anchorage section of the prosthetic part is dynamically and firmly connected to the end of the thighbone. After they have healed into the bone, prosthetic parts of this type which can be implanted without the use of cement are so firmly connected to the bone that removal which may possibly become necessary often necessitates opening of the sections of the cortical substance of the bone adjacent to the anchorage section.

By means of the present invention a prosthetic part is to be developed further in such a way that removal of the prosthetic part from the thighbone is possible without removing parts of the cortical substance.

In accordance with the invention this object is achieved by means of a prosthetic part having the features specified in claim 1 or 6.

In the case of the prosthetic part according to the invention, passages are present or can easily be created by removing webs of material located beneath indentations or by drilling the supporting plate free, through which passages a chisel or a slender milling cutter can be guided. In this way a slit can be produced in the section of the spongy substance adjacent to the cortical substance, as a result of which the cohesion between the spongy substance that has grown into the cage structure and the cortical substance is weakened. The bridges of spongy substance leading to the cortical substance that cannot be removed by the chisel or by the milling cutter can then be broken up by mechanical loading of the prosthetic part (e.g., impact and/or twisting, with application of considerable force). After this, the prosthetic part can be taken out of the bone.

Advantageous further developments of the invention are specified in the subordinate claims.

In the case of a prosthetic part the volume of spongy substance that has grown in is separable from the cortical substance of the bone on the two principal surfaces.

The further development of the invention permits an incision to be produced in the volume of spongy substance which may extend practically over the entire surface of contact with the cortical substance. In this way it is possible for the prosthetic part to be removed in a straightforward manner.

The further development of the invention is advantageous with regard to particularly rapid opening of the depression, whereby a secure and load-bearing connection of the edge of the plate section to the interior of the plate section is guaranteed by virtue of the depressions that have only slight depth. In the depressions having only slight depth the web of material can be removed by means of a milling cutter, whereby the walls of the depression may serve as a guide for the milling cutter.

The further development of the invention permits the setting angle of the chisel or milling cutter which is introduced into an opening or into an opened depression to be varied.

In the case of a prosthetic part a drill for drilling free the points of attachment of the anchorage pillars pertaining to the cage structure can be simply and precisely aligned with the axis of an anchorage pillar.

The invention is elucidated in more detail below on the basis of embodiments with reference to the drawing. Shown in the latter are:

Figure 1:
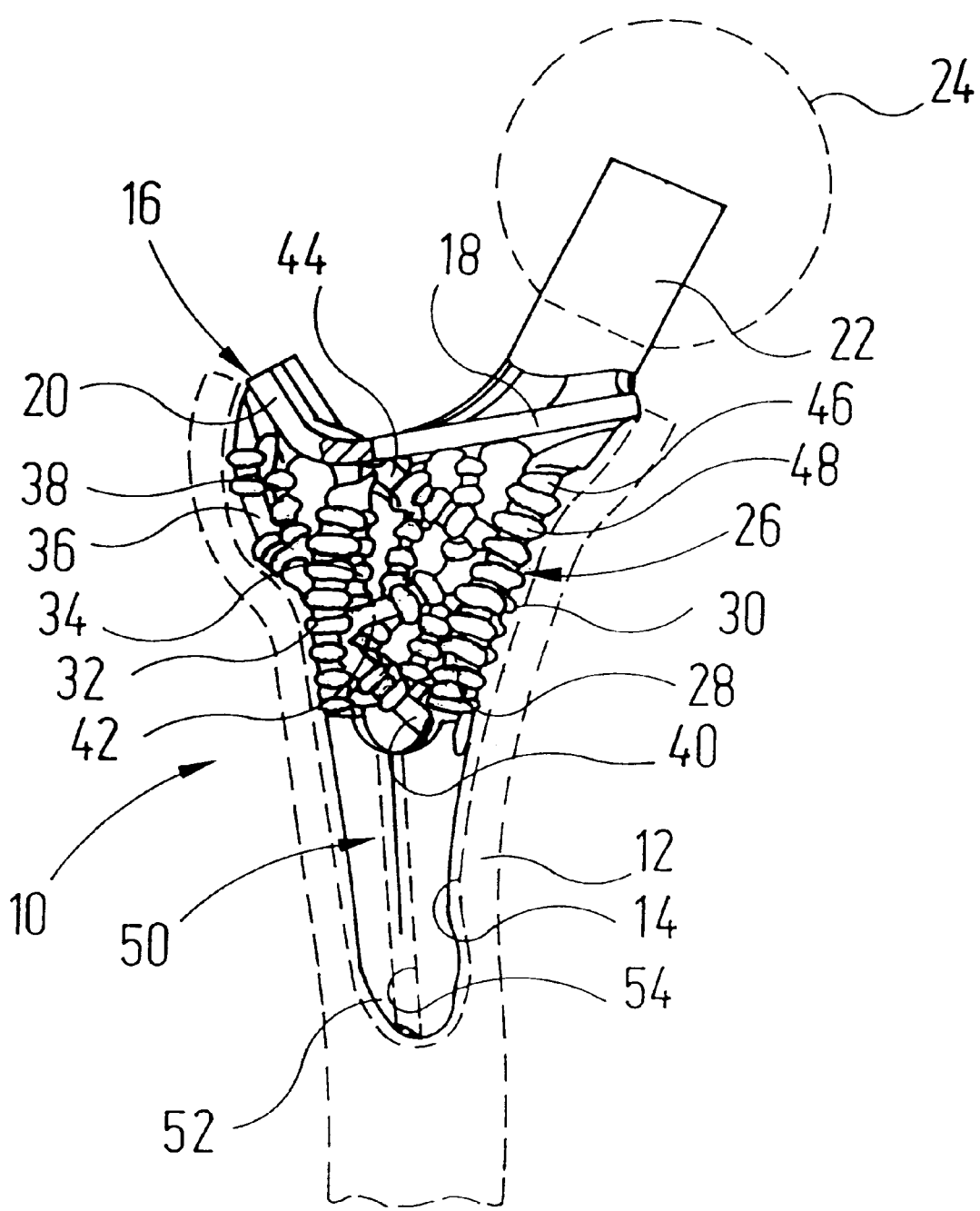
FIG. 1 is a lateral view of a prosthetic part for an artificial hip joint.

Designated overall by 10 in FIG. 1 is a prosthetic part which serves for implantation into the upper end of a thighbone 12 indicated by a dashed line. To this end the upper section of the thighbone 12 which bears the condyle is resected and a recess 14 corresponding to the clear outer contour of the prosthetic part 10 is produced in the thighbone.

The prosthetic part has a supporting plate 16 which comprises a horizontal plate section 18 and a plate section 20 ascending obliquely upwards to the trochanter major. Moulded onto the plate section 18 is a trunnion 22 ascending obliquely upwards, onto which a condyle 24 indicated by a dashed line is capable of being mounted.

Cast onto the underside of the supporting plate 16 is a cage structure which is designated overall by 26. This cage structure consists of four curved longitudinal anchorage pillars 28, 30, 32, 34 which substantially predetermine the shape of a curved pyramid having a rectangular transverse cross-section. From the upper end of the plate section 18 there emanate two curved additional anchorage pillars 36, 38, the configuration of which is adapted to the trochanter major of the thighbone (femur) and which have a smaller spacing from one another than the adjacent anchorage pillars 32 and 34.

In the interior of the clear contour of the cage structure 26 predetermined by the anchorage pillars 28–38 additional anchorage stiffening pillars are provided which extend in oblique directions between the anchorage pillars 28–38. Three such stiffening pillars 40, 42, 44 are shown.

The anchorage pillars and the stiffening pillars each have a cylindrical core 46 with axially spaced anchorage collars 48.

The cores 46 of the anchorage pillars typically have a diameter of 2.0–4.5 mm, the diameters of the anchorage collars are each about 0.8–1.5 mm larger than the diameter of the cores. The axial extent of the anchorage collars amounts to about 0.6–1.2 mm, their spacing from one another amounts to about 3–6 mm.

For the stiffening pillars the cores may have a diameter of about 1.5–3 mm, the diameters of the anchorage collars may be about 0.6–1.2 mm larger than the core diameter, and the axial dimension of the anchorage collars may amount to about 0.5–1 mm, their axial spacing to about 2–4 mm.

Cast onto the lower end of the cage structure 26 is a shaft section 50. The latter has an olive-shaped end section 52. A drill hole 54 extends through the interior of the shaft section 50.

With a view to implanting the prosthetic part described above, the end of the thighbone is resected as described above, the upper edge of the cortical substance being given a contour corresponding to the marginal contour of the supporting plate 16. The bone material removed from the end of the bone in the course of preparation of the recess 14 is ground in a bone mill and poured into the cage structure 26. The outer surface of the shaft section 50 is coated with a cement. The prosthetic part 10 is then inserted into the end of the thighbone 12, so that the supporting plate 16 now forms a new upper termination for the bone. The prosthetic part 10 is then temporarily fixed with wire.

After the cement has hardened, the prosthetic part 10 is connected to the upper end of the thighbone in partially loadable manner. In the further healing process the ground spongy substance coalesces and fills out the cage structure, at the same time growing up against the cortical substance and residues of spongy substance that have remained on the cortical substance.

Alternatively, the shaft section 50 may not be coated with cement, a possibility which is advantageous with regard to easier later removal of the prosthetic part.

After the healing process has been concluded an adhesive connection consequently exists between the outer surface of the shaft section 50 and the cortical substance of the thighbone, whereas in the region of the cage structure 26 there is an uninterrupted volume of spongy substance which has grown around the cage structure 26.

After the spongy substance has grown into the cage structure 26 a very firm and loadable connection exists between the thighbone and the prosthetic part. If for some reason the prosthetic part should have to be removed from the thighbone at any time, this would probably necessitate removing a part of the cortical substance surrounding the cage structure 26 and chiseling the cage structure 26 free again with a chisel through the window that has been created in this way. This would considerably restrict the options for a replacement prosthetic part, in particular it would rule out replacement by means of a prosthetic part that has to be cemented in.

Figure 2:
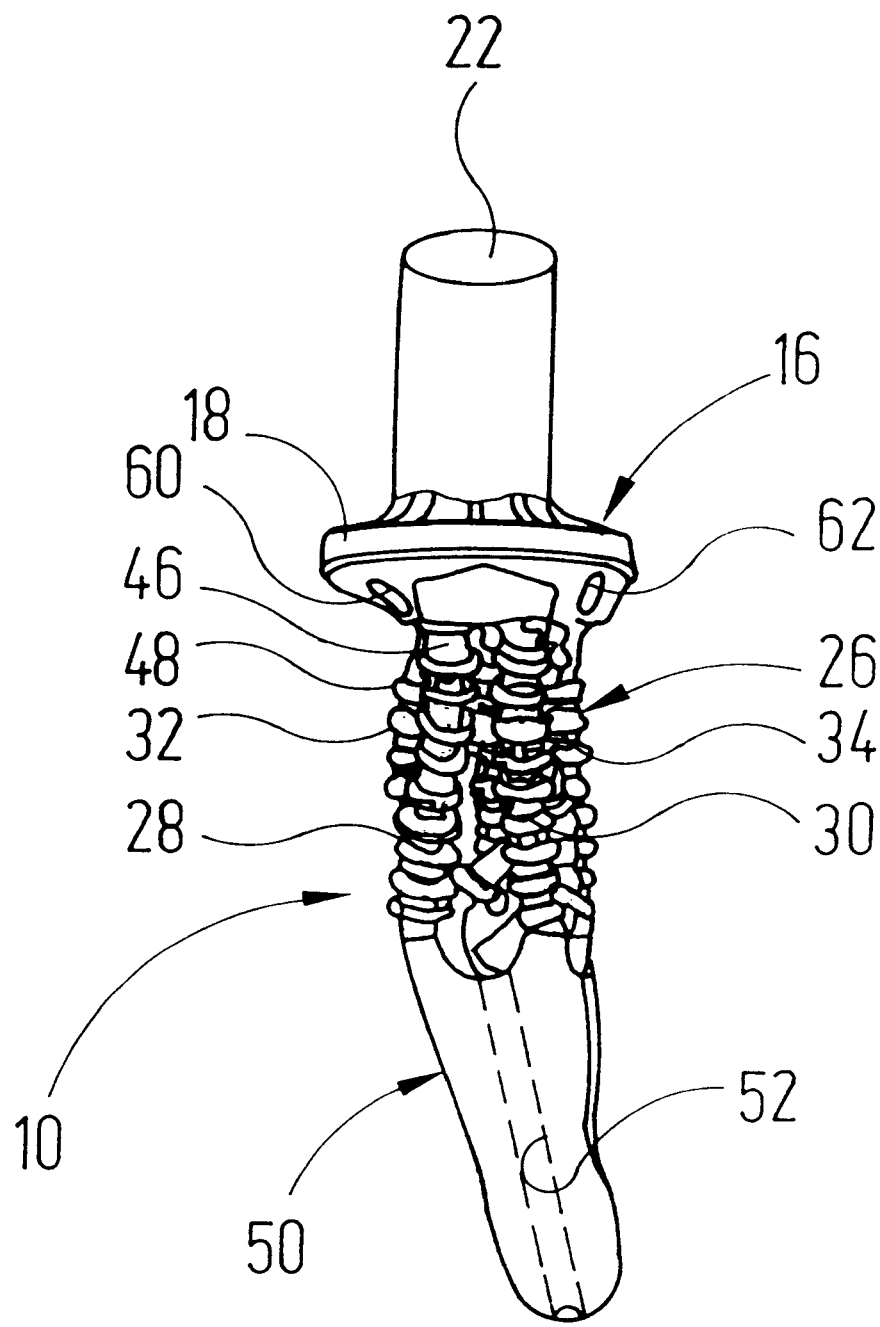
FIG. 2 is a view of the right side of the prosthetic part shown in FIG. 1.

In order to enable the cage structure 26 to be chiseled free without producing a window in the spongy substance, in the prosthetic part shown in FIGS. 1 and 2 elongated openings 60, 62 are provided in the vicinity of the longitudinal edges of the supporting plate 16. A thin, slender chisel can be guided through said openings after the prosthetic part 10 has healed in, in order in each case to chisel free one of the two principal surfaces of the cage structure 26. After such an operation to chisel the cage structure 26 free, bridges of spongy substance remain, via which the cage structure remains connected to the cortical substance in the vicinity of the upper corners of the supporting plate 16 and on the narrow sides of the cage structure. These remaining bridges can be broken open by rotating the prosthetic part 10 about the axis of the recess 14 and/or by inflicting severe blows on the supporting plate 16.

Figure 3:
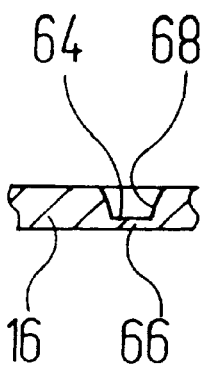
FIG. 3 is a transverse section through a depression which is provided in a near-edge region of a plate section of a modified prosthetic part.
Figure 4:
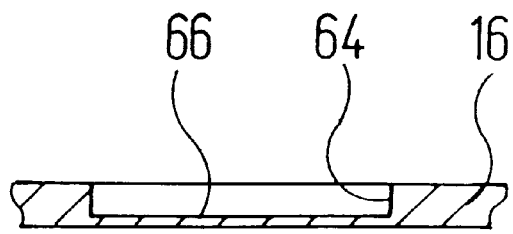
FIG. 4 is a longitudinal section through the depression provided in a near-edge region of a plate section of the modified prosthetic part according to FIG. 3.

If it is desired that the supporting plate 16 normally seals the upper end of the thighbone 12 completely but that access to the two principal surfaces of the cage structure 26 should nevertheless be possible, instead of openings it is possible, according to FIGS. 3 and 4, to work with indentations 64 in the supporting plate 16 which, seen in top view, have the same geometry as the openings 60, 62 shown in FIGS. 1 and 2. However, the indentations 64 have a thin bottom wall 66, which has the desired barrier effect, but on the other hand they can easily be mechanically destroyed by the chisel which serves to chisel the cage structure 26 free.

As is evident from FIG. 3, the lateral walls of the indentations 64 or of the openings that are later created from said indentations or of openings that are present from the very beginning are convex, as represented at 68. This permits the chisel or milling cutter which is used for chiseling the cage structure 26 free to be inclined also in the perpendicular direction relative to the longitudinal direction of the indentation or opening.

Figure 5:
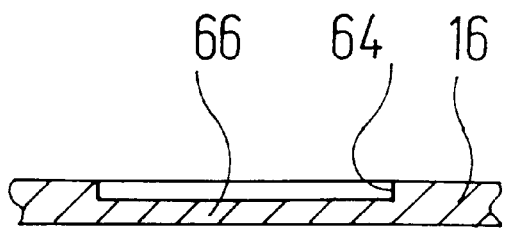
FIG. 5 is a similar view to FIG. 4 but wherein a depression having little depth is reproduced.

In a further modification, according to FIG. 5 use may be made of such indentations in which the bottom wall 66 makes up an appreciable part of the thickness of the supporting plate 16, so that the indentations 64 do not have a negative influence on the mechanical strength of the marginal region of the supporting plate 16. This design of the indentations 64 permits several such indentations to be distributed along the edge of the supporting plate 16, as a result of which a larger part of the interface between cage structure 26 and cortical substance of the thighbone 12 is made accessible. With such a design of the indentations 64 removal of the bottom wall 66 is effected by means of a milling cutter of suitable width, said milling cutter being guided by the walls of the indentation 64 parallel to the edge of the supporting plate 16.

Figure 6:
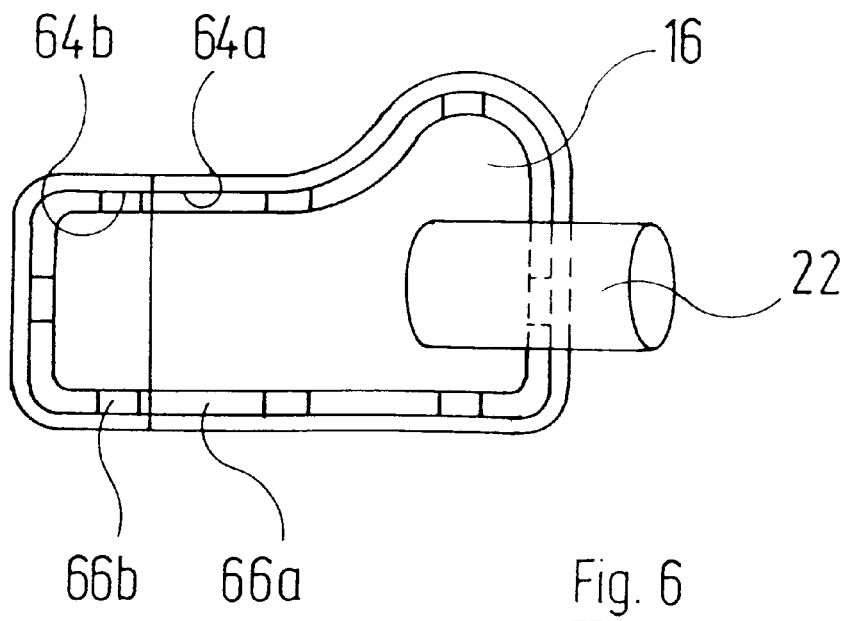
FIG. 6 is a top view of the plate section of a further modified prosthetic part which is provided in the marginal region of the plate section with a succession of depressions of differing depths.

In a further modification of the invention, according to FIG. 6 an arrangement of indentations 64a and 64b may be provided on the upper side of the supporting plate 16 continuously following the edge, the bottom walls 66a and 66b of said indentations being thin and thick, respectively. The bottom wall of the entire indentation arrangement can then be opened rapidly by means of a milling cutter which once again is positively guided parallel to the edge of the supporting plate 16 by the walls of the indentations, but under usage conditions a very loadable connection formed by the bottom walls 66b exists between the edge of the supporting plate 16 and the principal section thereof.

Figure 7:
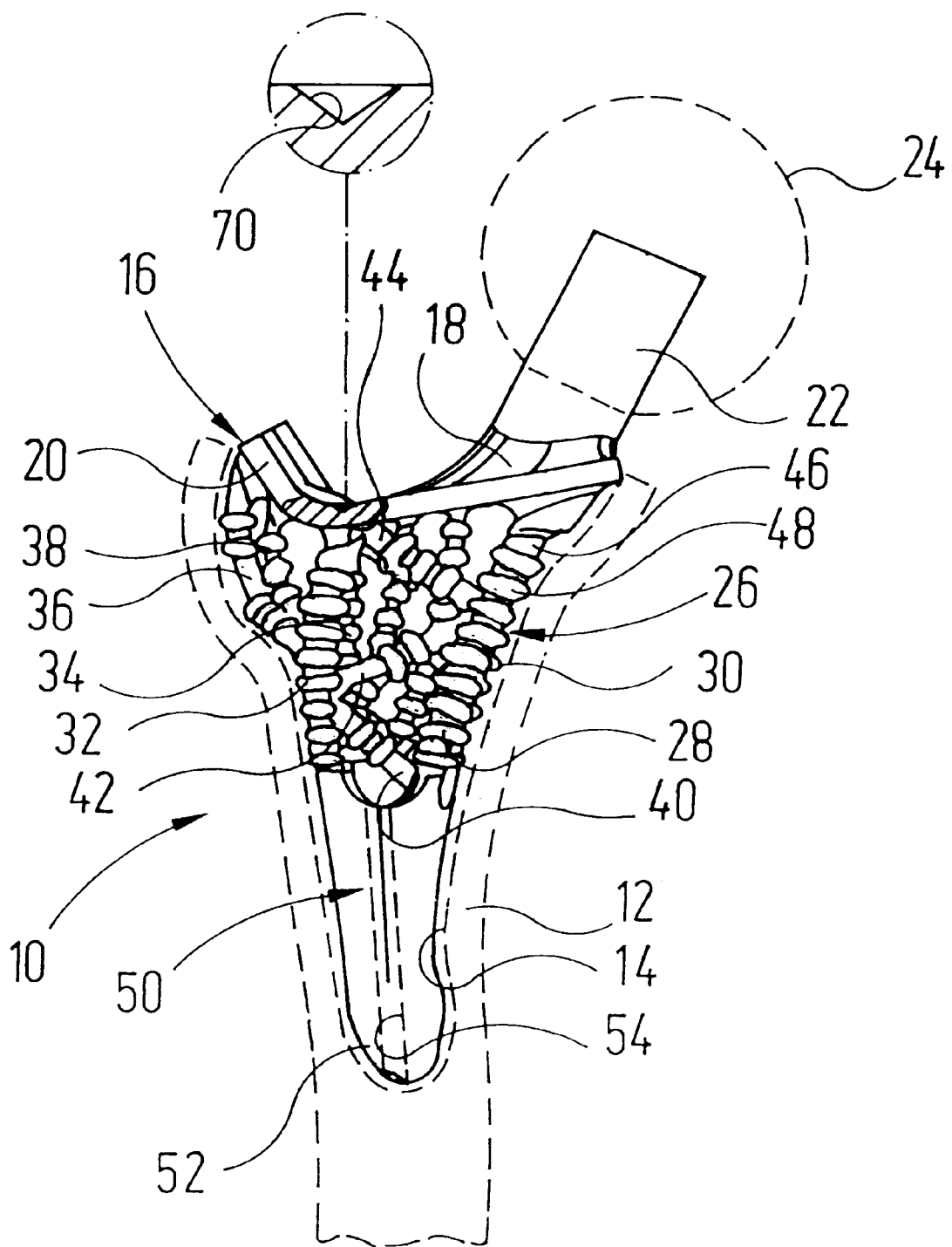
FIG. 7 is a view similar to FIG. 1, wherein a further modified prosthetic part is shown.

In the case of the prosthetic part 10 according to FIG. 7 all the base-points of anchorage pillars which emanate from the supporting plate 16 are marked by a conical marker 70 on the upper side of the supporting plate 16. These markers serve at the same time as centring holes for the point of a drill with which the material pertaining to the supporting plate located above these anchorage pillars can be drilled away. Once this has been done for all the anchorage pillars the supporting plate 16 comes free from the cage structure (thin webs of material possibly left standing can be broken in the course of drilling by progress of the drill), so that said cage structure can be simply chiseled or milled out of the recess 14.

What is claimed is:

1. A prosthetic part comprising
   an anchorage section (26, 50) that is introducable into a bone recess (14), said anchorage section comprising at least partially a cage structure (26),
   a plate section (16) which extends in a lateral direction beyond the anchorage section (26, 50), and
   a supporting section (22) for a joint part (24),
   wherein the plate section (16) is provided on its upper side with markers (70) which are each aligned with a supporting-plate attachment-point of an anchorage pillar (28 to 34) pertaining to the cage structure(26).

2. The prosthetic part as set forth in claim 1, wherein the markers comprise notches (70) which center a drill-point.

3. A prosthetic part comprising
   an anchorage section (26, 50) that is introducible into a bone recess (14), said anchorage section comprising at least partially a cage structure (26),
   a plate section (16) which extends in a lateral direction beyond the anchorage section (26, 50), and a supporting section (22) for a joint part (24), wherein the plate section (16) is provided with at least one opening (60, 62) or at least one indentation (64) in the vicinity of the edges of the plate section, through which a severing instrument is introducible to cut a connection between the anchoring section and corticalis substance of a bone, wherein the plate section (16) comprises a marginal region having a circumferential arrangement of indentations (64a, 64b), and, wherein the circumferential arrangement of indentations (64a, 64b) comprises a succession of indentations (64a, 64b) of differing depths.

4. The prosthetic part as set forth in claim 3, wherein the at least one opening (60, 62) or the at least one indentation (64) is convex.

5. The prosthetic part as set forth in claim 3, wherein the openings (60, 62) or the indentations (64) are convex.

6. The prosthetic part as set forth in claim 3, wherein the circumferential arrangement of indentations (64a, 64b) comprises a succession of indentations (64a, 64b) of differing depths.

* * * * *